US011369713B2

(12) United States Patent
Li et al.

(10) Patent No.: US 11,369,713 B2
(45) Date of Patent: Jun. 28, 2022

(54) DEGRADABLE AND ABSORBABLE HEMOSTATIC FIBER MATERIAL, PREPARATION METHOD THEREFOR, AND HEMOSTATIC FIBER ARTICLE THEREOF

(71) Applicant: Medprin Regenerative Medical Technologies Co., Ltd., Guangzhou (CN)

(72) Inventors: Guangyao Li, Guangdong (CN); Linjing Li, Guangdong (CN); Kunxue Deng, Guangdong (CN); Yuyu Yuan, Guangdong (CN)

(73) Assignee: Medprin Regenerative Medical Technologies Co., Ltd., Shanghai (CN)

( * ) Notice: Subject to any disclaimer, the term of this patent is extended or adjusted under 35 U.S.C. 154(b) by 278 days.

(21) Appl. No.: 16/345,560

(22) PCT Filed: Nov. 14, 2017

(86) PCT No.: PCT/CN2017/110959
§ 371 (c)(1),
(2) Date: Apr. 26, 2019

(87) PCT Pub. No.: WO2018/090913
PCT Pub. Date: May 24, 2018

(65) Prior Publication Data
US 2019/0314543 A1 Oct. 17, 2019

(30) Foreign Application Priority Data

Nov. 15, 2016 (CN) .......................... 201611004985.0

(51) Int. Cl.
*A61L 15/28* (2006.01)
*A61L 15/64* (2006.01)
*A61L 26/00* (2006.01)
*A61L 15/62* (2006.01)

(52) U.S. Cl.
CPC .............. *A61L 15/28* (2013.01); *A61L 15/64* (2013.01); *A61L 26/0023* (2013.01); *A61L 15/62* (2013.01); *A61L 26/009* (2013.01); *A61L 2400/04* (2013.01)

(58) Field of Classification Search
CPC .......... A61L 15/28; A61L 15/62; A61L 15/64; A61L 2400/04; A61L 26/0023; A61L 26/009
See application file for complete search history.

(56) References Cited

U.S. PATENT DOCUMENTS

| 7,262,181 B2 | 8/2007 | Zhang et al. |
| 2009/0291912 A1* | 11/2009 | Tijsma ................ A61K 31/718 514/55 |
| 2010/0298264 A1 | 11/2010 | Zhou et al. |

FOREIGN PATENT DOCUMENTS

| CN | 101890179 A | * 11/2010 | |
| CN | 103074699 A | * 5/2013 | ....... A61F 13/00012 |
| CN | 103120802 A | 5/2013 | |

OTHER PUBLICATIONS

Pier Lucio Anelli, Carlo Biffi, Fernando Montanari and Silvio Quici, "Fast and Selective Oxidation of Primary Alcohols to Aldehydes or to Carboxylic Acids and of Secondary Alcohols to Ketones Mediated by Oxoammonium Salts under Two-Phase Conditions", Journal of Organic Chemistry 1987, 52, 2559-2562. (Year: 1987).*
Pier Lucio Anelli, Stefano Banfi, Fernando Montanari and Silvio Quici, "Oxidation of Diols with Alkali Hypochlorites Catalyzed by Oxammonium Salts under Two-Phase Conditions", Journal of Organic Chemistry 1989, 54, 2970-2972. (Year: 1989).*
International Preliminary Report on Patentability, dated May 21, 2019, (7 pages).

\* cited by examiner

*Primary Examiner* — Mina Haghighatian
*Assistant Examiner* — Nathan W Schlientz
(74) *Attorney, Agent, or Firm* — Sheppard Mullin Richter & Hampton LLP (57) ABSTRACT

A degradable and absorbable hemostatic fiber material, a preparation method therefor, and a hemostatic fiber article thereof. The carboxylation degree of the hemostatic fiber material is 10-25%, and the polymerization degree of the hemostatic fiber material is 10-250. The hemostatic fiber material comprises fiber filaments, the linear density of the fiber filament being 0.8-4.5 dtex, and the dry strength of the fiber filament being 10-150 cN/tex. The degradable and absorbable hemostatic fiber material has a higher carboxylation degree and a lower polymerization degree, while the strength and completeness of the fiber filament can be well maintained, such that the hemostatic effect is better and the hemostasis is faster. Further, the hemostatic fiber material can be degraded and absorbed, and thus is safer.

17 Claims, 2 Drawing Sheets

DEGRADABLE AND ABSORBABLE HEMOSTATIC FIBER MATERIAL, PREPARATION METHOD THEREFOR, AND HEMOSTATIC FIBER ARTICLE THEREOF

CROSS REFERENCE TO RELATED APPLICATIONS

The present application is the U.S. National Stage Application under U.S.C. § 371 of PCT/CN2017/110959, filed Nov. 14, 2017, which claims priority to Chinese Patent Application No. 201611004985.0, filed Nov. 15, 2016, each of which is incorporated herein by reference in its entirety into the present disclosure.

FIELD OF THE INVENTION

The present disclosure relates to a degradable and absorbable hemostatic fiber material, preparation methods therefor, and hemostatic fiber products thereof, and belongs to the field of implantable medical materials.

BACKGROUND OF THE INVENTION

Hemostatic materials generally can be divided into non-degradable hemostatic materials and degradable hemostatic materials. Non-degradable hemostatic materials (such as commonly used ordinary gauze, bacterial cellulose dressings, etc.) are typically used to stop bleeding on the body surface. When a non-biodegradable hemostatic material is used for hemostasis in vivo, the material needs to be removed after use; otherwise, a prolonged contact with the wound tends to cause severe foreign body sensation. On the other hand, a biodegradable hemostatic material is generally obtained by modifying cellulose fibers. However, the modified cellulose fibers should also have suitable degrees of polymerization and carboxylation. Otherwise, the cellulose fibers are difficult to be degraded through human metabolism and deposit in certain organs, thereby damaging organ functions.

The Patent Document U.S. Pat. No. 3,364,200A discloses a method for oxidation of cellulose fibers using a nitrogen dioxide organic solution having a high concentration, which can lower the degree of polymerization of the original fiber material; however, it is difficult to control the degree of oxidation, and it tends to cause excessive oxidation of the fibers, such that the fibers become brittle and fracture, thereby affecting hemostasis.

The Patent Document CN104587517A discloses a preparation process for an absorbable hemostatic material made of regenerated cellulose fibers, which uses cyclohexane as a solvent to dissolve 1 to 3% nitrogen dioxide for oxidation. CN102018990A discloses a method for preparing oxidized cellulose hemostat products, which uses viscose fiber filament fabric as a raw material and oxidizes the fabric in an organic oxidizing solvent system. While the two methods improve the degradation and hemostatic effects of regular cellulose fibers to a certain extent, both use an organic solvent as a medium, the solubility of nitrogen dioxide in the organic solvent is low, the time for cellulose oxidation is long, and the oxidation is poor; moreover, the cost is high, the waste gas recovery is difficulty, and it is easy to cause air pollution.

In addition, the Patent Document CN1338475A discloses using a TEMPO-NaClO—NaBr oxidation system to oxidize cellulose fibers. Although the process of this patent can achieve a satisfactory degree of oxidation in a short time, it is necessary to control the pH value of the reaction solution in a range from 9 to 11 by adding an alkaline solution from time to time. The operation is complicated, and samples prepared using this method experience severe degradation and fracture, leading to a high loss of strength.

SUMMARY OF THE INVENTION

Problems to be Solved by the Present Invention

The present disclosure provides a degradable and absorbable hemostatic fiber material, a preparation method therefor, and a hemostatic fiber product thereof. The degradable and absorbable hemostatic fiber material according to the present disclosure achieves a high degree of carboxylation for the hemostatic fiber material, lowers the degree of polymerization for the hemostatic fiber material, and can better preserve the strength and integrity of fiber filaments.

Furthermore, the present disclosure also provides a preparation method for a degradable and absorbable hemostatic fiber material, which achieves a simple and easy preparation process and makes it unnecessary to control the pH value of the solution during the oxidation process.

The Solutions Used for Solving the Problems

The present disclosure provides a degradable and absorbable hemostatic fiber material, wherein the hemostatic fiber material has a degree of carboxylation of 10-25%, preferably 12-20%, and a degree of polymerization of 10-250, preferably 20-150; the hemostatic fiber material comprises fiber filaments having a linear density of 0.8-4.5 dtex, preferably 1.2-3 dtex; and the fiber filaments have a dry strength of 10-150 cN/tex, preferably 15-120 cN/tex.

The present disclosure provides a degradable and absorbable hemostatic fiber material, wherein the hemostatic fiber material has a maximum water absorption that is above 10 times, preferably 15-20 times, of the weight of the hemostatic fiber material.

The present disclosure further provides a hemostatic fiber product, comprising the degradable and absorbable hemostatic fiber material according to the present disclosure.

With regard to the hemostatic fiber product according to the present disclosure, more than 50% by quantity, preferably 60-85% by quantity, of the fiber filaments of the hemostatic fiber material have a length greater than 10 mm.

The hemostatic fiber product according to the present disclosure comprises a fiber layer of the hemostatic fiber material. Preferably, the hemostatic fiber product comprises 1-15 layers, preferably 4-10 layers, of the fiber layer, and more preferably, the thickness per fiber layer is 0.25-1 mm, preferably 0.4-0.8 mm.

With regard to the hemostatic fiber product according to the present disclosure, the fabric weight ratio per fiber layer is $1 \times 10^{-3}$-$8 \times 10^{-3}$ g/cm$^2$, preferably $1.5 \times 10^{-3}$-$3 \times 10^{-3}$ g/cm$^2$.

With regard to the hemostatic fiber product according to the present disclosure, the hemostatic fiber material in the hemostatic fiber product has a porosity above 50%, preferably 70-90%.

The hemostatic fiber product according to the present disclosure has softness of 100-1500 mN, preferably 400-800 mN.

The present disclosure further provides a preparation method for the degradable and absorbable hemostatic fiber material according to the present disclosure, the method comprising the following steps:

a step of carboxylation: performing activation processing on a fiber raw material, and then conducting a carboxylation reaction in a chloroacetic acid solution to obtain a carboxylated fiber; and a step of oxidation: placing the carboxylated fiber in a mixed solution of TEMPO-sodium bromide—an organic solvent-water, then adding sodium hypochlorite, and conducting an oxidation reaction to obtain the hemostatic fiber material.

With regard to the preparation method for the degradable and absorbable hemostatic fiber material according to the present disclosure, the activation processing comprises: placing the fiber raw material in an alkaline solution for activation processing, preferably, the alkaline solution comprising one or two of a sodium hydroxide solution and a potassium hydroxide solution.

With regard to the preparation method for the degradable and absorbable hemostatic fiber material according to the present disclosure, the chloroacetic acid solution is obtained by dissolving chloroacetic acid in a mixed solvent formed by water and an alcohol, preferably, the alcohol comprising one or more of methanol, ethanol, propanol, and isopropanol.

With regard to the preparation method for the degradable and absorbable hemostatic fiber material according to the present disclosure, the mass concentration of chloroacetic acid in the chloroacetic acid solution is 5-35%, preferably 10-20%.

With regard to the preparation method for the degradable and absorbable hemostatic fiber material according to the present disclosure, in the step of oxidation, the volumetric ratio of water to the organic solvent in the mixed solution of TEMPO-sodium bromide—the organic solvent-water is 1:0.5-2, preferably 1:0.5-1; the mass ratio of TEMPO to sodium bromide to the mixed solvent of water and the organic solvent is 1: 10-20:30-3000.

With regard to the preparation method for the degradable and absorbable hemostatic fiber material according to the present disclosure, in the step of oxidation, the mass ratio of TEMPO to sodium bromide to the carboxylated fiber to the sodium hypochlorite solution is 1: 10-20:30-100: 100-800, preferably 1: 10-15:30-50: 150-250.

With regard to the preparation method for the degradable and absorbable hemostatic fiber material according to the present disclosure, in the step of oxidation, the organic solvent comprises one or more of acetone, petroleum ether, dimethyl sulfoxide, dimethylformamide, and 1,4-dioxane.

The preparation method for the degradable and absorbable hemostatic fiber material according to the present disclosure further comprises a post-processing step for cleaning, centrifuging, and/or oven-drying the hemostatic fiber material.

The present disclosure further provides a preparation method for the hemostatic fiber product according to the present disclosure, the method comprising willowing, and/or carding, and/or lapping, and/or cutting the hemostatic fiber material to obtain the hemostatic fiber product.

The present disclosure further provides an application of the degradable and absorbable hemostatic fiber material according to the present disclosure in preparation of hemostatic cotton, hemostatic gauze, hemostatic non-woven cloth, hemostatic glue, hemostatic powder, hemostatic sponge, and hemostatic fiber membrane.

Effects Achieved by the Invention

The degradable and absorbable hemostatic fiber material according to the present disclosure achieves a high degree of carboxylation and a low degree of polymerization, and meanwhile, can excellently preserve the strength and integrity of fiber filaments, such that the hemostatic effect is better and faster. Moreover, the hemostatic fiber material according to the present disclosure is degradable and absorbable, and thus is safer.

Furthermore, the preparation method for the degradable and absorbable hemostatic fiber material according to the present disclosure omits the requirement by the prior art for a step to strictly control the pH value of the oxidizing system, leading to simpler and more convenient operations.

In addition, the present disclosure further provides a hemostatic fiber product, wherein the fiber layers of the hemostatic fiber product are independent of each other and can be readily separated. A doctor can control the amount of the hemostatic fiber product to be used according to the wound situation, which is convenient and fast.

DESCRIPTION OF THE SPECIFIC EMBODIMENTS

The present disclosure provides a degradable and absorbable hemostatic fiber material, wherein the hemostatic fiber material has a degree of carboxylation of 10-25%, preferably 12-20%, the hemostatic fiber material has a degree of polymerization of 10-250, preferably 20-150, and the hemostatic fiber material comprises fiber filaments having a linear density of 0.8-4.5 dtex, preferably 1.2-3 dtex; the fiber filaments have a dry strength of 10-150 cN/tex, preferably 15-120 cN/tex; when the linear density of the fiber filaments is in the range of 0.8-4.5 dtex, the fiber filaments have high strength and resilience, as well as good flexibility, which favors attachment to a wound and achieves a better hemostatic effect.

Preferably, the maximum water absorption of the hemostatic fiber material is above 10 times, preferably 15-20 times, of the weight of the hemostatic fiber material.

When the degree of carboxylation of the hemostatic fiber material is in the range of 12-20%, a better hemostatic effect can be achieved. When the degree of polymerization of the hemostatic fiber material is in the range of 10-250, the hemostatic fiber material can be easily degraded and metabolized by human body, will not deposit in some organs, and will thus not cause damages to organ functions. While achieving fast degradation and absorption, the hemostatic fiber material according to the present disclosure does not make the material to become rigid and brittle, and does not affect the hemostatic effect.

In addition, the degradable and absorbable hemostatic fiber material according to the present disclosure has high maximum water absorption and stronger affinity to water and/or saline solution. The hemostatic fiber material can rapidly absorb water in blood and will not dissolve. After water absorption, the hemostatic fiber material still has adhesion and will not be flushed away or penetrated. Therefore, the hemostatic fiber material according to the present disclosure not only can promote blood concentration, increase the viscosity, and slow down the blood flow to achieve the goal of effective hemostasis, but also can maintain excellent attachment to a wound even after water absorption.

The present disclosure further provides a hemostatic fiber product, comprising the degradable and absorbable hemostatic fiber material according to the present disclosure. The hemostatic fiber product according to the present disclosure comprises a fiber layer of the hemostatic fiber material. Preferably, the hemostatic fiber product comprises 1-15 layers, preferably 4-10 layers, of the fiber layer. For example, the hemostatic fiber product according to the present disclosure may be a membrane structure having fiber layers.

The hemostatic fiber product according to the present disclosure may have one single layer or multiple layers, and the fiber layers can be readily separated from each other. A doctor can control the amount of the hemostatic fiber product to be used according to the wound situation. For example, during use, the hemostatic fiber product that has multiple layers (e.g., 2 to 15 layers) may be separated and placed flatly on a wound to rapidly achieve the hemostatic effect. In addition, during use, the hemostatic fiber product that has a multi-layer structure may be placed on a location to stop the bleeding. When the bleeding is stopped, one or more layers of the hemostatic fiber product on the top that have not been in contact with the wound can be peeled off.

With regard to the hemostatic fiber product according to the present disclosure, more than 50% (percent by quantity), preferably 60-85% (percent by quantity), of the fiber filaments of the hemostatic fiber material have a length greater than 10 mm. When the length of the fiber filaments that form the hemostatic fiber product is maintained to be greater than 10 mm, the entanglement and knot formation among the fiber filaments are facilitated, which effectively prevents the fiber filaments from falling off during the use of the hemostatic fiber product.

With regard to the hemostatic fiber product according to the present disclosure, the fabric weight ratio per fiber layer is $1 \times 10^{-3}$-$8 \times 10^{-3}$ g/cm$^2$, preferably $1.5 \times 10^{-3}$-$3 \times 10^{-3}$ g/cm$^2$, and the thickness per fiber layer is 0.25-1 mm, preferably 0.4-0.8 mm.

With regard to the hemostatic fiber product according to the present disclosure, the hemostatic fiber material in the hemostatic fiber product has a porosity above 50%, preferably 70-90%.

The hemostatic fiber product according to the present disclosure has softness of 100-1500 mN, preferably 400-800 mN.

The hemostatic fiber product has excellent tissue compatibility, is soft and thin, facilitates operations such as wrapping, coating, plugging, etc., and is capable of in vivo degradation and absorption. Moreover, the hemostatic fiber product has high porosity and excellent breathability, which can simultaneously facilitate blood absorption and further improve the hemostatic effect. Therefore, the hemostatic fiber product according to the present disclosure can be applied to bleeding surgical wounds and sites where it is difficult to stop the bleeding.

The present disclosure further provides a preparation method for the degradable and absorbable hemostatic fiber material according to the present disclosure, the method comprising the following steps:

a step of carboxylation: performing activation processing on a fiber raw material, and then conducting a carboxylation reaction in a chloroacetic acid solution to obtain a carboxylated fiber; and a step of oxidation: placing the carboxylated fiber in a mixed solution of TEMPO-sodium bromide—an organic solvent-water, then adding sodium hypochlorite, and conducting an oxidation reaction to obtain the hemostatic fiber material.

The fiber raw material is, for example, cellulose fiber, which is a polymer with glucose as the unit and has a molecular formula of $(C_6H_{10}O_5)_n$. Due to the presence of a large quantity of hydroxy groups on the molecular chain of the cellulose fiber, the cellulose fiber forms a large quantity of intra-molecular and inter-molecular hydrogen bonds, and is gathered, in the solid state, into crystalline fibrillar structures of different levels, such that most of the highly reactive hydroxyl groups are enclosed within crystal regions, thereby leading to the heterogeneity of cellulose fibers in carboxylation and oxidation reactions. As a result, the performance of reaction products is directly impacted.

Primary hydroxyl groups and secondary hydroxyl groups in macromolecule rings of the cellulose fibers have different reactivities, and secondary hydroxyl groups have better reactivities under basic conditions. Therefore, the cellulose fibers may be subject to activation processing before reaction. For example, the fiber raw material is placed in an alkaline solution for activation processing, thereby improving the reaction speed, reaction degree, and reaction uniformity of the cellulose fibers in various chemical reactions.

With regard to the preparation method for the hemostatic fiber material according to the present disclosure, the alkaline solution in the step of carboxylation comprises one or more of a sodium hydroxide solution and a potassium hydroxide solution. The mass concentration of the sodium hydroxide solution or the potassium hydroxide solution is 20-55%, preferably 30-40%.

With regard to the preparation method for the hemostatic fiber material according to the present disclosure, in the step of carboxylation, the activation processing temperature is −5-50° C., preferably 10-30° C., and the activation processing time is 1-10 h, preferably 2-5 h; the carboxylation reaction temperature is 20-70° C., and the carboxylation reaction time is 2-12 h.

With regard to the preparation method for the hemostatic fiber material according to the present disclosure, the chloroacetic acid solution is obtained by dissolving chloroacetic acid in a mixed solvent of water and an alcohol, wherein the percent by volume of the alcohol in the mixed solvent of water and the alcohol is 50-90%, preferably 70-90%; the alcohol comprises one or more of methanol, ethanol, propanol, and isopropanol. The mixed solvent of water and an alcohol is a mixed solvent consisting of water and the alcohol.

In the present disclosure, the method to calculate the percent by volume of the alcohol is as follows: weigh the volume of the alcohol, add water to fix the volume to a certain volume, and the percent by volume of the alcohol is a ratio of the volume of the alcohol to the fixed volume. For example, 70% ethanol is obtained by using 70 mL ethanol and fixing the volume to 100 mL, i.e., the percent by volume of ethanol is 70%.

Using a mixed solvent consisting of water and an alcohol to dissolve chloroacetic acid facilitates the prevention of excessive swelling and dissolution of fibers, and consequently, better preserves the integrity and strength of the fibers.

With regard to the preparation method for the hemostatic fiber material according to the present disclosure, the mass concentration of the chloroacetic acid solution is 5-35%, preferably 10-20%.

With regard to the preparation method for the hemostatic fiber material according to the present disclosure, in the step of oxidation, the volumetric ratio of water to the organic solvent in the mixed solution of TEMPO-sodium bromide—the organic solvent-water is 1:0.5-2, preferably 1:0.5-1; the mass ratio of TEMPO to sodium bromide to the mixed solvent of water and the organic solvent is 1: 10-20:30-3000, wherein the volumetric ratio of water to the organic solvent may be a volumetric ratio prior to the mixing.

With regard to the preparation method for the hemostatic fiber material according to the present disclosure, in the step of oxidation, the organic solvent comprises one or more of acetone, petroleum ether, dimethyl sulfoxide, dimethylformamide, and 1,4-dioxane.

When an oxidation system of the mixed solution of TEMPO-sodium bromide—the organic solvent-water is used, i.e., when the organic solvent and water are used to replace pure water as the solvent of the TEMPO-NaClO—NaBr oxidation system, there is no need to control the pH value of the reaction solution, while the cellulose fibers can still be very well oxidized, and the strength and integrity of the cellulose fibers can be better preserved.

With regard to the preparation method for the hemostatic fiber material according to the present disclosure, in the step of oxidation, the sodium hypochlorite is preferably added in the form of a sodium hypochlorite solution, wherein the mass concentration of the sodium hypochlorite solution is 5-15%, preferably 8-10%.

With regard to the preparation method for the hemostatic fiber material according to the present disclosure, in the step of oxidation, the mass ratio of TEMPO to sodium bromide to the carboxylated fiber to the sodium hypochlorite solution is 1: 10-20:30-100: 100-800, preferably 1: 10-15:30-50: 150-250.

With regard to the preparation method for the hemostatic fiber material according to the present disclosure, in the step of oxidation, the oxidation reaction temperature is 0-25° C., preferably 2-10° C., and the oxidation reaction time is 2-48 h, preferably 2-15 h.

In the step of oxidation, the higher the oxidation processing temperature is, the faster the reaction rate is, and the shorter the reaction time becomes; however, side reactions may also be accelerated at the same time, and an overly high temperature may thus affect the proceeding of the oxidation reaction. Conversely, if the time is lower than 0° C., the reaction rate is slow, and the utilization rate of the mixed solution of TEMPO-sodium bromide—the organic solvent-water is low.

The preparation method for the hemostatic fiber material according to the present disclosure further comprises a post-processing step for cleaning, centrifuging, and/or oven-drying the hemostatic fiber material.

Preferably, the cleaning comprises cleaning with an ethanol solution or an isopropanol solution.

The present disclosure further provides a preparation method for the hemostatic fiber product according to the present disclosure, the method comprising willowing, and/or carding, and/or lapping, and/or cutting the hemostatic fiber material to obtain the hemostatic fiber product. A more suitable manner, such as a non-woven apparatus, may be selected as needed to prepare the hemostatic fiber product.

The present disclosure further provides an application of the hemostatic fiber material according to the present disclosure in preparation of hemostatic cotton, hemostatic gauze, hemostatic non-woven cloth, hemostatic glue, hemostatic powder, hemostatic sponge, and hemostatic fiber membrane.

The method of determining degree of carboxylation according to the present disclosure is as follows: cutting a sample to be determined into pieces, precisely weighing 500 mg of the sample, placing the sample in a 125 mL Erlenmeyer flask, adding 50 mL of a 2% calcium acetate solution, waiting for the sample to be determined to be fully immersed in the calcium acetate solution, mixing and stirring for 30 min, adding one drop of a phenolphthalein indicator, titrating with a sodium hydroxide titration solution (0.1 mol/L), and using a blank to calibrate the titration result. 1 mL of the sodium hydroxide titration solution is equivalent to 4.502 mg carboxyl group (—COOH).

The method of determining softness according to the present disclosure is as follows: a sum of the maximum vectors of anti-bending force of the product and the friction force between the product and a gap as determined according to the method of GB/T8942-2002, expressed in mN (millinewton). A lower softness value indicates that the fiber product is softer.

The method of determining porosity according to the present disclosure is as follows: the porosity of a sample to be determined is calculated according to the following equation, $$\theta = \left(1 - \frac{m}{V \cdot \rho s}\right) \times 100\%$$

Wherein m is the mass of a specimen (g);
V is the volume of the specimen (cm$^3$);
$\rho s$ is the skeletal density of the specimen material (g/cm$^3$) or is referred to as the true density.

EXAMPLES

The implement solutions of the present disclosure will be described below in detail with reference to examples. However, those skilled in the art shall understand that the following examples are only used to describe the present disclosure and should not be deemed as limitations to the scope of the present disclosure. In the case where no specific conditions are provided in the examples, conventional conditions or conditions suggested by manufacturers shall be followed. In the case where no manufacturer is noted for a reagent or instrument used, the reagent or instrument may be a conventional product purchased from the market.

Example 1

Place 1.5 kg cellulose fiber in a sodium hydroxide solution having a mass concentration of 20% for 4 h of activation at 30° C. After centrifugation, place the activated cellulose fiber in 50 L chloroacetic acid solution having a mass concentration of 20% for carboxylation, wherein the solvent of the chloroacetic acid solution is a mixed solvent of water and ethanol, and the percent by volume of ethanol in the mixed solvent of water and ethanol is 70%. For the carboxylation reaction, the reaction temperature is 70° C., and the reaction time is 5 h. After the reaction ends, take out the cellulose fiber, clean the cellulose fiber with an ethanol solution having a percent by volume of ethanol at 50% until the soaking solution becomes neutral, and obtain a carboxylated fiber.

Dissolve 25 g TEMPO and 400 g sodium bromide in 70 L of an aqueous solution of dimethylformamide, wherein the volumetric ratio of water to dimethylformamide in the aqueous solution of dimethylformamide is 1:1, and obtain a mixed solution of TEMPO-sodium bromide-dimethylformamide-water.

Place the carboxylated fiber in the mixed solution of TEMPO-sodium bromide-dimethylformamide-water, disperse the carboxylated fiber homogeneously, then add 4.5 kg of a sodium hypochlorite solution having a mass concentration of 5% in batches, control the temperature of the reaction system at 10° C., and conduct an oxidation reaction. After the oxidation reaction is completed, add 300 mL anhydrous ethanol to terminate the reaction, then clean and dry the oxidized cellulose fiber, and obtain a hemostatic fiber material I. Then, use a non-woven apparatus to sequentially perform willowing, carding, and lapping to obtain a hemostatic fiber product I.

Example 2

Place 1 kg cellulose fiber in a sodium hydroxide solution having a mass concentration of 50% for 2 h of activation at 30° C. After centrifugation, place the activated cellulose fiber in 40 L chloroacetic acid solution having a mass concentration of 15% for carboxylation, wherein the solvent of the chloroacetic acid solution is a mixed solvent of water and isopropanol, and the percent by volume of isopropanol in the mixed solvent is 50%. For the carboxylation reaction, the reaction temperature is 55° C., and the reaction time is 7 h. After the reaction ends, take out the cellulose fiber, clean the cellulose fiber with an ethanol solution having a percent by volume of ethanol at 50% until the soaking solution becomes neutral, and obtain a carboxylated fiber.

Dissolve 35 g TEMPO and 350 g sodium bromide in 50 L of an aqueous solution of 1,4-dioxane, wherein the volumetric ratio of water to 1,4-dioxane in the aqueous solution of 1,4-dioxane is 1:0.5, and obtain a mixed solution of TEMPO-sodium bromide-1,4-dioxane-water.

Place the processed cellulose fiber in the mixed solution of TEMPO-sodium bromide-1,4-dioxane-water, disperse the processed cellulose fiber homogeneously, then add 4 kg of a sodium hypochlorite solution having a mass concentration of 8% in batches, conduct an oxidation reaction, and control the reaction temperature at 15° C. After the oxidation reaction is completed, add 200 mL anhydrous ethanol to terminate the reaction, then clean and dry the fiber filaments, and obtain a hemostatic fiber material II. Then, use a non-woven apparatus to sequentially perform willowing, carding, and lapping to obtain a hemostatic fiber product II.

Example 3

Place 1 kg cellulose fiber in a sodium hydroxide solution having a mass concentration of 30% for 2 h of activation at 30° C. After centrifugation, place the activated cellulose fiber in 40 L chloroacetic acid solution having a mass concentration of 20% for carboxylation, wherein the solvent of the chloroacetic acid solution is a mixed solvent of water and ethanol, and the percent by volume of ethanol in the mixed solvent is 90%. For the carboxylation reaction, the reaction temperature is 70° C., and the reaction time is 5 h. After the reaction ends, take out the cellulose fiber, clean the cellulose fiber with an ethanol solution having a percent by volume of ethanol at 50% until the soaking solution becomes neutral, and obtain a carboxylated fiber.

Dissolve 25 g TEMPO and 300 g sodium bromide in 10 L of an aqueous solution of petroleum ether, wherein the volumetric ratio of water to petroleum ether in the aqueous solution of petroleum ether is 1:2, and obtain a mixed solution of TEMPO-sodium bromide-petroleum ether-water.

Place the processed cellulose fiber in the mixed solution of TEMPO-sodium bromide-petroleum ether-water, disperse the processed cellulose fiber homogeneously, then add 3 kg of a sodium hypochlorite solution having a mass concentration of 15% in batches, control the temperature of the reaction system at 3° C., and conduct an oxidation reaction. After the oxidation reaction is completed, add 300 mL anhydrous ethanol to terminate the reaction, then clean and dry the fiber filaments, and obtain a hemostatic fiber material III. Then, use a non-woven apparatus to sequentially perform willowing, carding, and lapping to obtain a hemostatic fiber product III.

Example 4

Place 1.5 kg cellulose fiber in a sodium hydroxide solution having a mass concentration of 25% for 5 h of activation at 20° C. After centrifugation, place the activated cellulose fiber in 50 L chloroacetic acid solution having a mass concentration of 25% for carboxylation, wherein the solvent of the chloroacetic acid solution is a mixed solvent of water and ethanol, and the percent by volume of ethanol in the mixed solvent is 80%. For the carboxylation reaction, the reaction temperature is 50° C., and the reaction time is 8 h. After the reaction ends, take out the cellulose fiber, clean the cellulose fiber with an ethanol solution having a percent by volume of ethanol at 50% until the soaking solution becomes neutral, and obtain a carboxylated fiber.

Dissolve 40 g TEMPO and 500 g sodium bromide in 40 L of an aqueous solution of dimethylformamide, wherein the volumetric ratio of water to dimethylformamide in the aqueous solution of dimethylformamide is 1:1, and obtain a mixed solution of TEMPO-sodium bromide-dimethylformamide-water.

Place the carboxylated fiber in the mixed solution of TEMPO-sodium bromide-dimethylformamide-water, disperse the carboxylated fiber homogeneously, then add 3 kg of a sodium hypochlorite solution having a mass concentration of 10% in batches, control the temperature of the reaction system at 2° C., and conduct an oxidation reaction. After the oxidation reaction is completed, add 300 mL anhydrous ethanol to terminate the reaction, then clean and dry the oxidized cellulose fiber, and obtain a hemostatic fiber material IV. Then, use a non-woven apparatus to sequentially perform willowing, carding, and lapping to obtain a hemostatic fiber product IV.

Example 5

Place 1 kg cellulose fiber in a sodium hydroxide solution having a mass concentration of 40% for 3 h of activation at 30° C. After centrifugation, place the activated cellulose fiber in 50 L chloroacetic acid solution having a mass concentration of 10% for carboxylation, wherein the solvent of the chloroacetic acid solution is a mixed solvent of water and isopropanol, and the percent by volume of isopropanol in the mixed solvent is 65%. For the carboxylation reaction, the reaction temperature is 30° C., and the reaction time is 6 h. After the reaction ends, take out the cellulose fiber, clean the cellulose fiber with an ethanol solution having a percent by volume of ethanol at 50% until the soaking solution becomes neutral, and obtain a carboxylated fiber.

Dissolve 20 g TEMPO and 250 g sodium bromide in 30 L of an aqueous solution of 1,4-dioxane, wherein the volumetric ratio of water to 1,4-dioxane in the aqueous solution of 1,4-dioxane is 1:0.5, and obtain a mixed solution of TEMPO-sodium bromide-1,4-dioxane-water.

Place the processed cellulose fiber in the mixed solution of TEMPO-sodium bromide-1,4-dioxane-water, disperse the processed cellulose fiber homogeneously, then add 2.5 kg of a sodium hypochlorite solution having a mass concentration of 5% in batches, conduct an oxidation reaction, and control the reaction temperature at 15° C. After the oxidation reaction is completed, add 200 mL anhydrous ethanol to terminate the reaction, then clean and dry the fiber filaments, and obtain a hemostatic fiber material V. Then, use a non-woven apparatus to sequentially perform willowing, carding, and lapping to obtain a hemostatic fiber product V.

Example 6

Place 1 kg cellulose fiber in a sodium hydroxide solution having a mass concentration of 30% for 3 h of activation at 30° C. After centrifugation, place the activated cellulose fiber in 30 L chloroacetic acid solution having a mass concentration of 20% for carboxylation, wherein the solvent of the chloroacetic acid solution is a mixed solvent of water and ethanol, and the percent by volume of ethanol in the mixed solvent is 90%. For the carboxylation reaction, the reaction temperature is 70° C., and the reaction time is 8 h. After the reaction ends, take out the cellulose fiber, clean the cellulose fiber with an ethanol solution having a percent by volume of ethanol at 50% until the soaking solution becomes neutral, and obtain a carboxylated fiber.

Dissolve 30 g TEMPO and 350 g sodium bromide in 50 L of an aqueous solution of petroleum ether, wherein the volumetric ratio of water to petroleum ether in the aqueous solution of petroleum ether is 1:2, and obtain a mixed solution of TEMPO-sodium bromide-petroleum ether-water.

Place the processed cellulose fiber in the mixed solution of TEMPO-sodium bromide-petroleum ether-water, disperse the processed cellulose fiber homogeneously, then add 3.5 kg of a sodium hypochlorite solution having a mass concentration of 10% in batches, control the temperature of the reaction system at 10° C., and conduct an oxidation reaction. After the oxidation reaction is completed, add 300 mL anhydrous ethanol to terminate the reaction, then clean and dry the fiber filaments, and obtain a hemostatic fiber material VI. Then, use a non-woven apparatus to sequentially perform willowing, carding, and lapping to obtain a hemostatic fiber product VI.

Comparison Example 1

Dissolve 25 g TEMPO and 240 g sodium bromide in 50 L water to obtain a mixed solution.

Place 0.5 kg cellulose fiber in the mixed solution, disperse the cellulose fiber homogeneously, and add a sodium hypochlorite solution having a mass concentration of 8% in four times with 2 L added each time. Control the temperature of the reaction system at 8° C., and conduct an oxidation reaction by adding an aqueous solution of sodium hydroxide to control the system pH at around 10.0. After the oxidation reaction is completed, pour the reaction liquid of the oxidation reaction into an excess amount of ethanol, immerse the precipitate in 0.01 mol/L HCl twice for 3 h each time, dry in vacuum at 40° C., and obtain a hemostatic fiber material VII. Then, use a non-woven apparatus to sequentially perform willowing, carding, and lapping to obtain a hemostatic fiber product VII.

Comparison Example 2

Place 1 g cellulose fiber in a sodium hydroxide solution having a mass concentration of 30% for 3 h of activation at 40° C.

After centrifugation, place the activated cellulose fiber in 40 L chloroacetic acid solution having a mass concentration of 20% for carboxylation, wherein the solvent of the chloroacetic acid solution is a mixed solvent of water and ethanol, and the percent by volume of ethanol in the mixed solvent is 70%. For the carboxylation reaction, the reaction temperature is 70° C., and the reaction time is 5 h. After the reaction ends, clean the cellulose fiber with an ethanol solution having a percent by volume of ethanol at 70% until the soaking solution becomes neutral, and obtain a carboxylated fiber, i.e., a hemostatic fiber material VIII. Then, use a non-woven apparatus to sequentially perform willowing, carding, and lapping to obtain a hemostatic fiber product VIII.

Table 1 lists performance parameters of the hemostatic fiber materials I-VIII prepared in Examples 1-6 and Comparison Examples 1-2 and the fiber raw material; Table 2 lists performance parameters of the hemostatic fiber products I-VIII prepared in Examples 1-6 and Comparison Examples 1-2 and the fiber raw material, wherein the non-woven apparatus is used to sequentially perform willowing, carding, and lapping on the fiber raw material to obtain a fiber product.

TABLE 1

|  | Degree of carboxylation (%) | Degree of polymerization | Dry strength (cN/tex) | Linear density (dtex) | Maximum water absorption (times) |
|---|---|---|---|---|---|
| Example 1 | 18 | 150 | 30 | 1.2 | 16.5 |
| Example 2 | 20 | 100 | 28 | 1.2 | 18 |
| Example 3 | 17 | 130 | 31 | 1.2 | 15 |
| Example 4 | 22 | 35 | 20 | 1.2 | 17 |
| Example 5 | 15 | 200 | 50 | 3 | 12 |
| Example 6 | 19 | 70 | 100 | 4.5 | 19 |
| Comparison Example 1 | 12 | 50 | 5 | 1.2 | 10 |
| Comparison Example 2 | 10 | 350 | 29 | 1.2 | 18 |
| Fiber raw material | 0 | 380 | 32 | 1.2 | 6 |
| Determination method |  | GB/T1548-2004 | GB/T14463-2008 | GB/T14335-2008 | YY/T0471.1-2004 |

It can be seen from Table 1 that, for the hemostatic fiber materials I-VI, the degree of carboxylation is in the range of 12-25%, the degree of polymerization is between 10 and 250, the linear density of the fiber filaments is in the range of 10-150 cN/tex, and the maximum water absorption is 15 to 20 times of the weight of the hemostatic fiber material. Compared with the hemostatic fiber materials VII-VIII in Comparison Examples 1-2 and the fiber raw material, the hemostatic fiber materials I-VI according to the present disclosure simultaneously have high degree of carboxylation and low degree of polymerization, and can better preserve the strength of fiber filaments. As a result, the hemostatic fiber materials according to the present disclosure not only achieve a good hemostatic effect, but also are easy to be degraded and metabolized by human body, and full degradation and absorption can be achieved. In addition, the hemostatic fiber materials I-VI according to the present disclosure are insoluble, and after water absorption, the hemostatic fiber materials have excellent adhesion and will not be flushed away or penetrated.

TABLE 2

|  | Number of layers (layer) | Fabric weight ratio (g/cm$^2$) | Porosity (%) | Softness (mN) | Length of fiber filaments (mm) |
| --- | --- | --- | --- | --- | --- |
| Example 1 | 10 | 0.003 | 86 | 756 | 20 |
| Example 2 | 10 | 0.0025 | 72 | 625 | 25 |
| Example 3 | 10 | 0.003 | 81 | 780 | 25 |
| Example 4 | 5 | 0.0020 | 88 | 750 | 27 |
| Example 5 | 5 | 0.0015 | 75 | 650 | 28 |
| Example 6 | 5 | 0.003 | 80 | 850 | 30 |
| Comparison Example 1 | 10 | 0.003 | 50 | 890 | 8 |
| Comparison Example 2 | 10 | 0.003 | 70 | 950 | 28 |
| Fiber raw material | 10 | 0.0025 | 75 | 820 | 38 |

It can be seen from Table 2 that the hemostatic fiber materials I-VI according to the present disclosure have a porosity above 50%, which achieves great breathability; has good softness, which facilitates attachment to a wound and achieves better hemostatic effect. In addition, more than 50% of the fiber filaments in the hemostatic fiber products I-VI have a length greater than 10 mm, which achieves high resilience and makes it difficult for the fiber filaments to break.

Hemostasis Experiments on Rabbit Liver Models

Shave the abdominal hair of the rabbits, perform standard median laparotomy, and dissociate and expose livers; cut off the liver tissue at about 1 cm from the tip of each lobe of the liver, and create active bleeding models; use the accurately weighed hemostatic fiber products and fiber raw material (at the same mass), respectively, to press on the wound until the bleeding is stopped, and record the bleeding time, as shown in Table 3.

It can be seen from Table 3 that the hemostatic fiber products I-VI according to the present disclosure stop bleeding in less than 5 min, the hemostatic speed is faster than that of the hemostatic fiber products VII-VIII and the fiber raw material, and the hemostatic effect is good.

Degradation and Absorption Experiments

Select 15 healthy rabbits, and divide the rabbits evenly into three groups that are numbered as Group 1, Group 2, and Group 3, respectively, wherein Group 1 is the experimental group, and Group 2 and Group 3 are control groups. Subject the rabbits to anesthesia through ear intravenous injection, and implant hemostatic materials in the rabbit abdomens, wherein the hemostatic fiber product I prepared in Example 1 of the present disclosure is implanted for the experimental group (Group 1), the fiber raw material that has not been modified is implanted for the control group (Group 2), and the hemostatic fiber product VII prepared in Comparison Example 1 is implanted for the control group (Group 3). After stitching and fixation, take care of the rabbits using antibiotics for three days after the surgery, and dissect the rabbits at weeks 1, 2, 4, 8, and 12 after the implantation for observation. Each time, one animal is randomly selected from each group for dissection, and samples are taken and fixed for histological observation.

Figure 1:
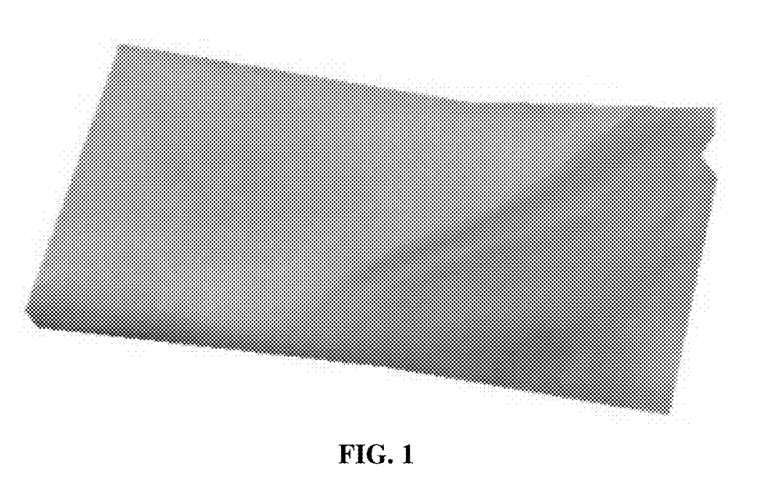
FIG. 1 is an overall view of a hemostatic fiber product prepared in Example 1 of the present disclosure.
Figure 2:
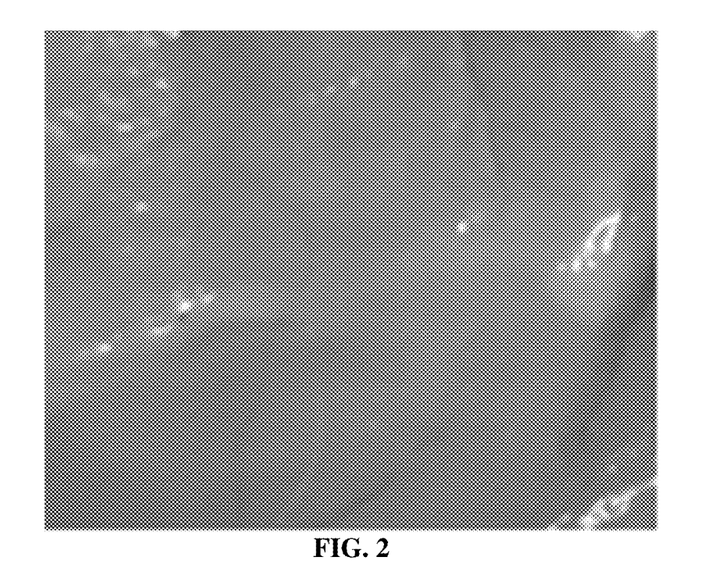
FIG. 2 illustrates in vivo degradation and absorption, after one week, of the hemostatic fiber product prepared in Example 1.
Figure 3:
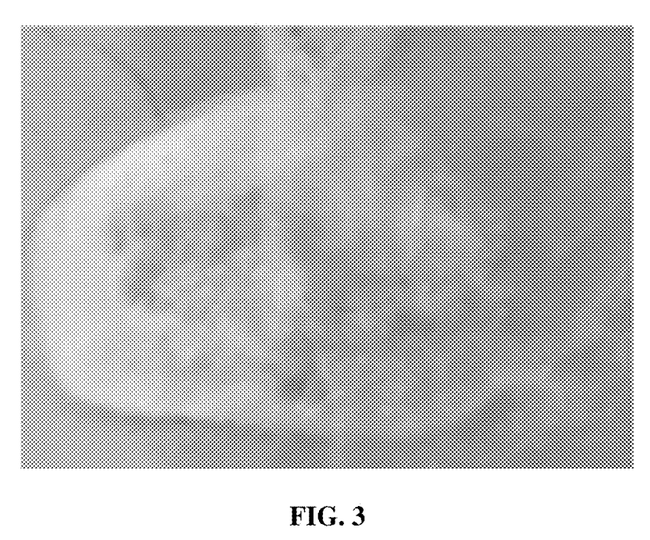
FIG. 3 illustrates in vivo degradation and absorption, after 2 months, of the fiber raw material.
Figure 4:
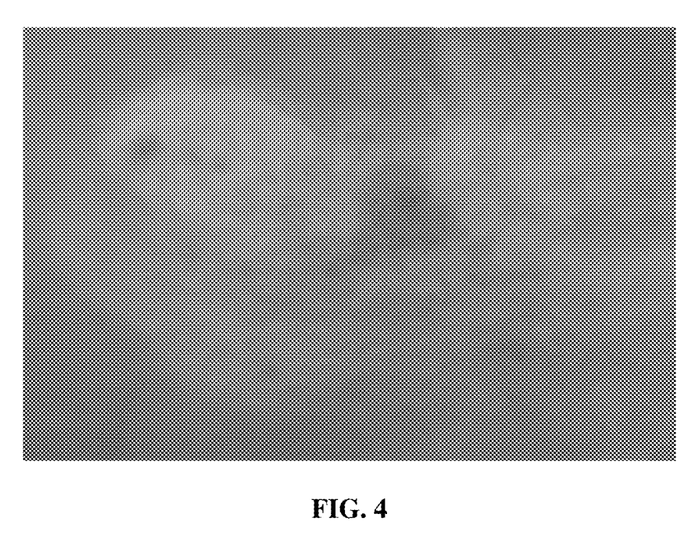
FIG. 4 illustrates in vivo degradation and absorption, after one week, of the hemostatic fiber product prepared in Comparison Example 1.

FIG. 2 illustrates in vivo degradation and absorption, after one week, of the hemostatic fiber product I prepared in Example 1; FIG. 3 illustrates in vivo degradation and absorption, after 2 months, of the fiber raw material; and FIG. 4 illustrates in vivo degradation and absorption, after one week, of the hemostatic fiber product VII prepared in Comparison Example 1. As shown in FIGS. 2-4, the hemostatic fiber product I in the experimental group (Group 1) was fully degraded within one week; the fiber raw material in the control group (Group 2) remained intact without degradation after one week, and the majority of the fiber raw material still existed after 2 months; the hemostatic fiber product VII in the control group (Group 3) still partially existed after one week.

TABLE 3

|  | Example 1 | Example 2 | Example 3 | Example 4 | Example 5 | Example 6 | Comparison Example 1 | Comparison Example 2 | Fiber raw material |
| --- | --- | --- | --- | --- | --- | --- | --- | --- | --- |
| Time to stop bleeding (min) | 3 | 2.6 | 3.25 | 4 | 3.5 | 3.8 | 8 | >10 | >10 |

In addition, the hemostatic fiber products II-VI prepared in Examples 2-6 of the present disclosure also achieve an effect of rapid degradation and absorption. Therefore, the hemostatic fiber products of the present disclosure achieve an effect of rapid degradation and absorption.

The above examples of the present disclosure are merely examples made for clearly describing the present disclosure, rather than limitations to the implementation manners of the present disclosure. Those skilled in the art may further make modifications or variations in other different forms based on the above description. There is no need, nor is it possible to exhaust all implementation manners herein. Any modification, equivalent substitution, and improvement made within the spirit and principle of the present disclosure shall be encompassed by the protection scope of the claims of the present disclosure.

The invention claimed is:

1. A method for preparing a degradable and absorbable hemostatic cellulose fiber material, wherein the method comprises:
   carboxylating a cellulose fiber raw material in a chloroacetic acid solution to obtain a carboxylated fiber; and
   oxidating the carboxylated fiber in an aqueous solution comprising water, TEMPO, sodium bromide, and an organic solvent, followed by addition of sodium hypochlorite, to obtain the hemostatic cellulose fiber material, wherein the organic solvent is selected from the group consisting of acetone, petroleum ether, dimethyl sulfoxide, dimethylformamide, and 1,4-dioxane wherein the hemostatic cellulose fiber material has a degree of carboxylation of 10-25% and a degree of polymerization of 20-150; the hemostatic cellulose fiber material comprises fiber filaments having a linear density of 1.2-3 dtex; and the fiber filaments have a dry strength of 10-150 cN/tex.

2. The method of claim 1, wherein the chloroacetic acid solution is obtained by dissolving chloroacetic acid in a mixed solvent of water and an alcohol.

3. The method of claim 2, wherein the alcohol comprises one or more of methanol, ethanol, propanol, or isopropanol.

4. The method of claim 1, wherein the volumetric ratio of water to the organic solvent in the aqueous solution is 1:0.5-2; and the mass ratio of TEMPO to sodium bromide to the mixed solvent of water and the organic solvent is 1:10-20:30-3000.

5. The method of claim 4, wherein the mass ratio of TEMPO to sodium bromide to the carboxylated fiber to the sodium hypochlorite solution is 1:10-20:30-100: 100-800.

6. The method of claim 1, further comprising cleaning, centrifuging, and/or oven-drying the hemostatic fiber material.

7. A degradable and absorbable hemostatic cellulose fiber material, prepared according to the method of claim 1.

8. The degradable and absorbable hemostatic fiber material of claim 7, wherein the hemostatic fiber material has a maximum water absorption that is more than 10 times of the weight of the hemostatic fiber material.

9. The degradable and absorbable hemostatic fiber material of claim 7, wherein the dry strength of the fiber filaments is 15-120 cN/tex.

10. A hemostatic fiber product, comprising the degradable and absorbable hemostatic fiber material of claim 7.

11. The hemostatic fiber product of claim 10, wherein more than 50% by quantity of the fiber filaments of the hemostatic fiber material have a length greater than 10 mm.

12. The hemostatic fiber product of claim 10, wherein the hemostatic fiber product comprises a fiber layer of the hemostatic fiber material.

13. The hemostatic fiber product of claim 12, wherein the fabric weight ratio per fiber layer is $1\times10^{-3}$-$8\times10^{-3}$ $g/cm^2$.

14. The hemostatic fiber product of claim 10, wherein the hemostatic fiber material in the hemostatic fiber product has a porosity greater than 50%.

15. The hemostatic fiber product of claim 10, wherein the hemostatic fiber product has softness of 100-1500 mN.

16. The hemostatic fiber product of claim 10, wherein 60-85%, by quantity, of the fiber filaments of the hemostatic fiber material have a length greater than 10 mm.

17. The hemostatic fiber product of claim 10, wherein the hemostatic fiber product comprises 1-15 layers of the fiber layer, and the thickness per fiber layer is 0.25-1 mm.

* * * * *

UNITED STATES PATENT AND TRADEMARK OFFICE
CERTIFICATE OF CORRECTION

| | | |
|---|---|---|
| PATENT NO. | : 11,369,713 B2 | Page 1 of 1 |
| APPLICATION NO. | : 16/345560 | |
| DATED | : June 28, 2022 | |
| INVENTOR(S) | : Guangyao Li et al. | |

It is certified that error appears in the above-identified patent and that said Letters Patent is hereby corrected as shown below:

On the Title Page

Assignee item (73) Line 2 delete "Shanghai" and insert --Guangzhou--

Signed and Sealed this
Twenty-seventh Day of December, 2022

Katherine Kelly Vidal
*Director of the United States Patent and Trademark Office*